United States Patent [19]

Lathrop et al.

[11] Patent Number: 5,133,352
[45] Date of Patent: Jul. 28, 1992

[54] METHOD FOR TREATING HERPES SIMPLEX

[75] Inventors: Peter H. Lathrop, San Diego, Calif.; Steve K. Johnston, Grand Island, Nebr.

[73] Assignee: Kent, Lathrop and Johnston, San Diego, Calif.

[21] Appl. No.: 508,840

[22] Filed: Apr. 12, 1990

[51] Int. Cl.$^5$ ............................................. A61N 1/20
[52] U.S. Cl. ............................................. 128/419 R
[58] Field of Search ................. 128/419 R, 421, 898, 128/362, 422

[56] References Cited

U.S. PATENT DOCUMENTS

| | | |
|---|---|---|
| 305,894 | 9/1884 | Clarke ............................ 128/419 R |
| 715,650 | 12/1902 | En Holm . |
| 1,433,184 | 10/1922 | Csanyi . |
| 4,010,742 | 3/1977 | Kim . |
| 4,037,590 | 7/1977 | Dohring et al. . |
| 4,040,414 | 8/1977 | Suroff . |
| 4,073,289 | 2/1978 | Fahim . |
| 4,095,601 | 6/1978 | Aufranc et al. . |
| 4,181,128 | 1/1980 | Swartz ............................ 128/362 |
| 4,269,176 | 5/1981 | Beyer et al. . |
| 4,309,989 | 1/1982 | Fahim . |
| 4,372,296 | 2/1983 | Fahim . |
| 4,484,569 | 11/1984 | Driller et al. . |
| 4,583,529 | 4/1986 | Briggs . |
| 4,646,725 | 3/1987 | Moasser . |
| 4,694,840 | 9/1987 | Kairis ............................ 128/419 R |
| 4,738,263 | 4/1988 | Seebach et al. . |
| 4,802,470 | 2/1989 | Hara et al. . |
| 4,846,178 | 7/1989 | Fuxue ............................ 128/422 |
| 4,913,148 | 4/1990 | Dietheln ....................... 128/419 R |

FOREIGN PATENT DOCUMENTS

| | | |
|---|---|---|
| 2558525 | 8/1976 | Fed. Rep. of Germany ... 128/419 R |
| 2507783 | 9/1976 | Fed. Rep. of Germany ...... 128/421 |
| 7900116 | 4/1980 | Netherlands ........................ 128/421 |

OTHER PUBLICATIONS

Bibliography—(attached to specification).
Oberdorfer Research Corporation Literature Search Report on Herpes Electrotherapy Treatment (enclosed).

Primary Examiner—Richard J. Apley
Assistant Examiner—Karen Ann Richard
Attorney, Agent, or Firm—Wall and Roehrig

[57] ABSTRACT

The present invention provides an apparatus and method for treating infectious skin conditions, such as Herpes Simplex 1 and 2. By the application of an electrical field and current to the area of the manifestation of the disease on the body there is activated a reaction at the cell level to combat the virus and disrupt its attack on the healthy cell structure. The present method comprises a direct application of a low voltage direct current, low amperage stimulation to the skin about the infected location for a few seconds every hour for a length of time sufficient to prevent formation and/or heal the resultant lesion.

14 Claims, 1 Drawing Sheet

METHOD FOR TREATING HERPES SIMPLEX

FIELD OF THE INVENTION

The present invention relates to a method and apparatus for treating infectious skin conditions, and more particularly to a method of treatment for prevention and therapeutic healing of herpesvirus infections at the cell level.

BACKGROUND OF THE INVENTION

Herpes Simplex is caused by herpesvirus homonomous types 1 and 2. Infections due to the virus are worldwide, and they are considered to be one of the most common sexually-transmitted diseases. Herpes Simplex affects 92 million Americans. Type 2 appears to be more neurogenic and accounts for about 80% of the genital infections. There is about a 60-80% risk of sexual passage of the infection in those repeatedly exposed to an infected conjugal partner, indicating that circulating antiviral antibodies, which rise fourfold following an outbreak, do not prevent superinfection. Type 1 Herpes Simplex is generally associated with infection in and around the mouth, and with other Herpes Simplex infections above the waist. Typically, it is characterized by a cluster of small blisters or watery vesicles on the skin or on mucus membranes. The lesions are commonly called cold sores or fever blisters. They most frequently occur on the lips and face and occasionally on the trunk and hands. The Type 1 virus may also infect the eye, causing corneal ulcers and visual impairment.

The occurrence of a lesion is often signalled by tingling with burning in the skin area, which becomes red and covered with vesicles. These vesicles break and form a crust. The skin appears normal within six to ten days after the onset of the lesion, unless there has been secondary infection. Lesions may often reappear at the same site for many years, and may be precipitated by any one of a number of factors, such as sunburn, upper respiratory and gastrointestinal tract infections, fevers, emotional stress, or anxiety.

Herpes Simplex Virus Type 2 is associated with genital infections. Herpes genital infections are most often transmitted through sexual contact. Sexual practices involving oral/genital contact may be responsible for some crossover infections, while other infections occur through hand/genital/mouth contacts. The incubation period for Herpes genital infection is usually four to five days, but may be as short as 24 hours and as long as two weeks. The first symptoms may be pain or itching at the site of infection. This is followed within a day or two by the appearance of blister-like lesions that may occur singularly or in groups. In males, the common sites of infection include the foreskin, the glans and the shaft of the penis. In females, the blister may occur on the labia, the clitoris, the opening of the vagina, or, occasionally, on the cervix. Within a few days, the blisters rupture and merge to form large areas of denuded tissue surrounded by swollen, inflamed skin. At this stage, the lesions may become exquisitely painful with intense burning and irritation. In females especially, urination may cause great discomfort. Generalized symptoms such as fever and malaise may develop, and lymph glands in the groin may enlarge. Lesions may persist at this stage for a week or more and complete healing may take four to six weeks. Genital herpes infections generally are more severe in females and may become so uncomfortable and disabling as to require hospitalization. Reoccurrences of herpes genital infection are not uncommon, and may be associated with emotional stress, trauma, intercourse, and other infections or menstruation. Symptoms may not be as severe in the recurrent infections as in the initial ones.

A variety of treatments have been used for genital herpes, but none has been entirely satisfactory. Drying agents such as alcohol, spirits of camphor, and ether have been used. Other methods of treatment include the use of ointments and creams, topical anesthetics, and antiseptic solutions. As of today, no satisfactory vaccine has been found. In superficial infections, topical agents such as Idoxuridine (IDU), Triflurothymidine, or Acyclovir are sometimes effective. General cleansing with soap and water is recommended, but keeping lesions moist may aggravate the inflammation and delay healing.

THE HERPESVIRUS

In general, viruses are the smallest infectious agents (20-300 nanometers in diameter), containing a molecule of nucleic acid (RNA or DNA) as the genome. Nucleic acid is encased in a protein shell. Viruses replicate only in living cells. The viral nucleic acid contains information necessary for programming the infected host cell to synthesize the number of specific macromolecules. Toward the end of the replicative cycle, more viral nucleic acids and coat proteins are produced. The coat proteins assemble together to form the symmetric protein shell which encloses the nucleic acid genome. These empty capsids are byproducts of the viral replicative cycle. The capsid encases and stabilizes the viral nucleic acid against the extracellular environment and facilitates the attachment, and perhaps penetration of the virus upon contact with new susceptible cells. The viral nucleocapsid, is about 100 nanometers in diameter, and possesses cubic symmetry with 162 capsomeres and is surrounded by a lipid containing envelope. The enveloped virion is 100 to 150 millimeters in diameter. Latent infections may occur and last for the life span of the host, even in the presence of circulating antibodies. The concept that herpesvirus persists in the nuclei of cells in the sensory ganglia suggests that any topical treatment will be ineffective in destroying the virus in these hidden locations.

The structural proteins of the herpesviruses have several important functions. They serve to protect the viral genome against inactivation by nuclei, participate in the attachment of the virus particle to a susceptible cell, and are responsible for the structural symmetry for the virus particle. Other proteins, which synthesize in infectious cells, include those which enable the viral nucleic acid to replicate and those which alter some function or structure of the host cell.

Approximately 25 viruses have been placed in the herpesvirus group. They all contain a core of double stranded DNA surrounded by a protein coat that exhibits isocahedril symmetry, which in turn is enclosed in an envelope which contains essential lipids.

The structural proteins of Herpes Simplex virus include nine polypeptides, which have been found in the enveloped virion, two polypeptides, which are associated with the envelope, two arginine polypeptides within the virus core, as well as guanine and cytosine.

The virus enters the cell either by fusion with the cell membrane or by pinocytosis. It is then uncoated, and the DNA becomes associated with the nucleus. Soon after infection, the virus codes for its own DNA polymerase and other enzymes such as thymidine kinase, which is associated with the DNA replication. Viral proteins are synthesized in the cytoplasm and are then transmitted to the nucleus for virus assembly.

INFECTION OF THE HEALTHY CELL WITH HERPESVIRUS

Herpesvirus nucleocapsids are assembled in the cell nucleus and acquire envelopes from the nuclear rather than the cytoplasmic membranes. Virus is assembled in the nucleus and approaches the nuclear membrane. At the point of contact, the inner nuclear membrane becomes thicker and progressively envelopes the virus particle. It finally pinches off, leaving the nuclear membrane intact and enveloped particle free in the perinuclear cisterna. Nucleocapsids may also acquire envelopes by budding into nuclear vacuoles. These vacuoles seem to be indentations of a nuclear membrane, and are continuous with the perinuclear cisterna.

The virus particle is now transported from the vicinity of the nucleus toward an extracellular location in the following sequence: the outer lamella of the nuclear envelope wraps around the enveloped nucleocapsid and sequesters it from the cell cytoplasm. When the vacuole reaches the cytoplasmic membrane, the enveloped virion is released outside the cell.

An additional route seems to be through the cisternae of the endoplasmic reticulum to the exterior of the cell. Later in the infection, unenveloped particles may also appear in the cytoplasm where they may be enveloped, but breaks in the nuclear membrane are also present at this time. The envelopment process occurs whenever the nucleocapsid comes into contact with a cell membrane and may represent a cellular defense mechanism. Since the nuclear membrane is the first membrane encountered, it would be the primary site of envelopment.

PRIOR ART

In the past, treatment for Herpes Simplex lesions has consisted primarily of topical application of drugs for symptomatic relief of Herpes lesions, such as analgesics and anesthetics for the relief of pain, which have had minimal therapeutic effect on the lesions. Also, various treatments involving painting of the lesions with acridine dyes, and then exposing them to ultraviolet light, have been tried without significant therapeutic effect, and with an associated risk of producing malignant cells.

More recently, it has been proposed to treat Herpes Simplex 1 and 2 with ultrasound, such as set forth in U.S. Pat. No. 4,646,725 issued Mar. 3, 1987, and U.S. Pat. No. 4,309,989 issued Jan. 12, 1982 wherein a method for massaging a medication into the skin by ultrasound is disclosed.

These suggested treatments have not found wide acceptance to date, and the present invention is directed toward a method and apparatus for a more therapeutic treatment involving cell stimulation by electrical and magnetic fields and the like. To aid in the understanding of the present invention, the following review of the neural/electrical systems of the body will be helpful.

THE ELECTRICAL CONTROL SYSTEM OF THE BODY

The human body and its physiological processes are made up of a universe of electrical activity. Chemical reactions involve electrical ion transfer, development of potential, electrostatic interaction, and changes in an electromagnetic field. Physiological processes are controlled by electrical interaction.

The body uses a capacitive state to generate a potential from which stored energy is used to run cellular processes. The cell membrane is an electric capacitor in which two conducting media, the intra-cellular and the extra-cellular salt solutions are separated by the non-conducting membrane. The electrical potential across the capacitor is proportional to the number of charges that are held on its plates. At this basic level, cell energy function can be manipulated electronically.

Damage to this system, in the form of a pathological or viral state, causes a current of injury to the overall electromagnetic environmental balance of the system. Laboratory research by applicant and others has shown that a negative charge acts as a trigger for healing growth control systems.

Becker, Robert O., *The Body Electric*, William Morrow, Inc., New York, NY (1985);

Black, Jonathon, *Tissue Response To Exogenous Electromagnetic Signals*, Orthopedic Clinics of North America, Vol. 15, No. 1 (1984); and Carley, Patrick J. and Stanley F. Warnapel, *Electrotherapy for Acceleration of Wound Healing: Low Intensity Direct Current*, Artc Phys Med Rehabil. Vol. 66 443–446 (1986).

Embryonic cells know which respective tissues to differentiate into, the nervous system uses electrical pathways for orientation of growth and regeneration, and this current is used in lower organisms for control of cellular differentiation and limb.

The cell membrane is made of a bi-layer of phospholipid sheets. A single phospholipid has a charged polar head group with a (hydrophobic) hydrocarbon tail. Two sheets of these asymmetric molecules, placed tail to tail, gives rise to a leaflet membrane with the polar heads facing out on both sides. The polar groups are hydrophilic and interact with the aqueous exterior/interior, thereby forcing the hydrophobic tails to interact and hold the membrane together. This hydrophobic core is at its lowest energy state which maintains this structure. Due to the charged groups on the outside and the hydrophobic groups inside, the membrane itself is impermeable to most molecules and ions which makes it an ideal organizational structure for a living mechanism. The cell may selectively determine what it allows in or out utilizing transport mechanisms.

An integral membrane protein (IMP) is a large molecule that spans the entire lipid-lipid bi-layer. Part of the protein is on the outside, extracytoplasmic surface. It crosses through the membrane interior and extrudes into the inside cytoplasmic portion of the cell. These proteins interact hydrophilicly on the outside on the extracytoplasmic and cytoplasmic sides with charged proteins while interacting with the non-polar interior with hydrophobic proteins. This insures their stability and direct orientation within the cell membrane. The IMP is a long string of amino acids and may span the membrane many times (by going back and forth as a thread may span a clothes seam) and in so doing, create a pore or channel in which ions or molecules may selectively pass.

Passage through the membrane of molecules and ions depends on a variety of factors such as concentration on both sides, electrical charge, membrane potential, and molecular size. The cell mediates transport through the IMP. Passive transport or simple diffusion is the process by which small, non-charged molecules "migrate" from a high concentration to a lower one or "down its concentration gradient." The rate limiting step is the movement through the hydrophobic interior of the membrane.

Facilitated diffusion is much faster than passive transport because it utilizes the IMP to create a pore/channel through which molecules may pass (therefore, the rate limiting exterior step is based on how it permeates the polar, then hydrophobic interior, etc.). The process is specific as to which ion or molecules may go through each channel. The rate of transport is determined largely by cellular concentration gradients and permeability of the channels. In certain cases, the permeability of these pores changes by external influence. One of these external influences is electrical current.

Active transport is the third mechanism by which the cell uses membrane proteins to regulate its environment and control species concentrations on either side of the cell. Active transport requires the absorption of energy to drive the transport of a molecule or ion. The transfer may go up or down the concentration gradient or may carry an ion across the membrane and hydrophobic interior. This is not possible by diffusion. The protein complex that accomplishes this reaction turns the stored energy of a molecule such as adenosine triphosphate (ATP) into a potential stored energy by forming a gradient of ions or molecules across the membrane. ATP is the energy currency of the cell, it has a highly exergenic bond of the third phosphate group. The reaction hydrolyzing this bond liberates energy which is used to fuel biochemical reactions. The formula being ATP $\longrightarrow$ ADP+Pi. An ATPase is an enzyme that catalyzes the hydrolysis of ATP.

This concentration gradient of charge for moving ions to one side or chemical for moving a solute such as sugar to the interior, that we develop, is a form of potential energy that can accomplish work for the cell. This is in accordance with conservation of energy i.e., energy in the form of ATP is converted to a chemical-/electrical gradient.

An integral membrane protein essential to the cell is the $Na+/K+ATPase$. The protein spans both sides of the plasma membrane creating a controlable gate with a chemical that separates the respective ions to either side of the membrane. The separation is in unequal concentrations and creates an electrochemical gradient or potential across the membrane. This unequal charge distribution has the property of capacitance and acts as a battery with a potential determined by ionic differences. Discharged distribution of stored energy is the basis of cellular control of biochemical processes and the primary function of our nervous system. Electric current profused through the tissues creates a force of electrically charged ions present at interfaces between different types of tissues and cell membranes. Conduction of current through the tissues depends on ionic movement.

When electrical currents are introduced into the body, ions accumulate at the tissue interfaces and at the cell membranes, creating a charge that is opposite to the charge at the voltage applied at the electrodes. The potential difference that occurs between each electrode and the tissue is created by an electrolytic polarization. This phenomenon occurs in living tissue, and is comparable to a conductor with capacitance.

OBJECTS AND SUMMARY OF THE INVENTION

It is an object of the present invention to provide a method and apparatus for treating infectious skin conditions which provide rapid and effective treatment of the infection.

It is another object of the present invention to provide a method and apparatus for preventing the formation of the Herpes Simplex lesions.

It is a further object of the present invention to provide a method and apparatus for disrupting the Herpes Simplex 1 and 2 virus attack at the cell level.

It is yet a further object of the present invention to stimulate the peripheral nervous system of the human body to alter its physiological processes in the area of the viral attack to disrupt the development of the virus cell as it attempts to infect healthy cells in the human body.

It is a still further object of the present invention to provide a method and apparatus for treating infectious skin conditions such as Herpes Simplex 1 and 2 in which an electrical current is used to radically change the response of healthy cells to the invading virus.

It is yet another object of the present invention to provide a method and apparatus for effective treatment of the Herpes Virus Simplex 1 and 2 by electrical stimulation at the site of a lesion before eruption of the actual lesion.

It is yet a further object of the present invention to provide a method and apparatus for treatment of Herpes Simplex 1 and 2 by electrical stimulation of healthy cells during the pre-lesion symptom phase indicated by tingling and the like to prevent formation of the virus lesions.

In one embodiment of the present invention this is accomplished by applying a low voltage direct current stimulation localized at the pre-lesion site, at the first indication of tingling or other irritating symptoms usual in an attack of Herpes Simplex 1 or 2.

BRIEF DESCRIPTION OF THE DRAWINGS

Further objects of the invention, together with additional features contributing thereto and advantages accruing therefrom will be apparent from the following description of a preferred treatment according to the invention and the apparatus shown in the accompanying drawings wherein.

DETAILED DESCRIPTION OF THE PREFERRED EMBODIMENT

Figure 1:
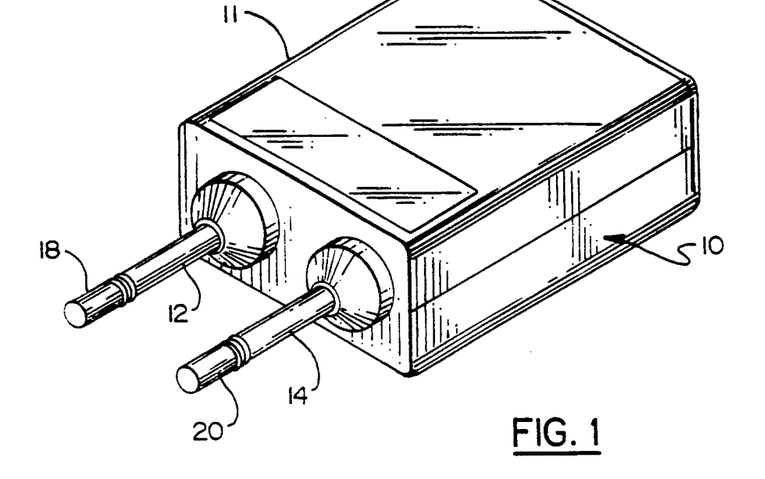
FIG. 1 is a perspective view of a device in accordance with the present invention.

Referring now to FIG. 1, there is shown an electrical stimulator 10, according to the present invention which consists of a housing containing the battery and other electrical components which are connected to the two spaced apart probes 12 and 14 which have electrically conductive metallic end caps 18 and 20 on the ends thereof connected electrically to the battery and other components within the case 10.

These probes typically are spaced apart one-half inch to one-and-a-half inches and extend one-half to one inch from the housing 11 of the stimulator so as to permit easy application to an area of the body where the Herpes Simplex lesions are likely to develop. The housing 11 and the probes, except for the metallic tip are made of an insulating material and are in a configuration that can be readily and easily gripped in the hand of the patient.

Figure 2:
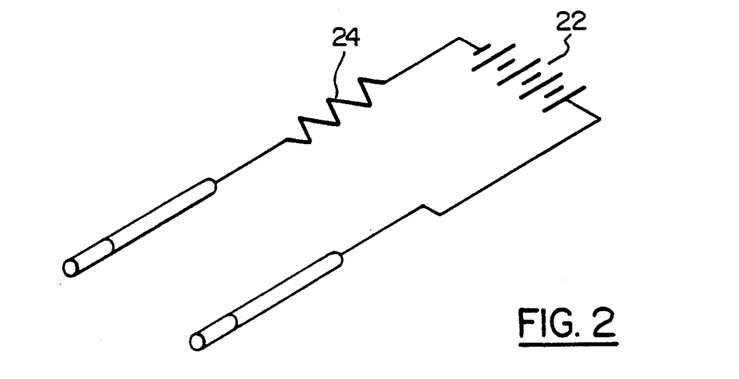
FIG. 2 is a circuit diagram of the electrical circuit of the device of FIG. 1.

Referring now to FIG. 2, the circuit for applying the voltage to the probes is shown and includes a nine volt battery 22 of any conventional type which provides a nine volt dc potential between the two probe tips and has a maximum current output of approximately 30 miliamps. A 330 ohm resistor 24 is placed in series with the battery to one lead to limit the current output to a desired level for cell stimulation as described in more detail herein. Other values may be used as required for a particular stimulation.

The device is used by applying the two metal tips of the probes to the body on either side of the area that contains the lesion or is being irritated as by tingling or pain or other indication of the onset of development of a lesion. The device should be applied as soon as possible after the onset of symptoms and preferably within the first fifteen minutes. The device is held to the skin in the affected area for approximately two to twenty seconds and this process is then repeated hourly for up to eight hours or longer if a lesion actually erupts. In the case where a lesion does develop, the procedure continues until healing. The specific duration and time intervals can be adjusted to best match a particular symptom.

While a battery operated portable device is shown a rectified low voltage from commercial power may be used, particularly in a clinic setting. For some applications, the stimulation may be machine pulsed rather than being physically applied and removed at specific intervals.

BEST MODE FOR CARRYING OUT THE INVENTION

The following explanation is believed to accurately depict the mechanism by which the treatment method of the present invention effects the observed beneficial therapeutic effect. Low voltage electrical current actually recharges the energy level of the cell which changes the biochemical working of the cell at micro levels. This has been shown in recent studies to increase ATP energy production by up to 500%, and increased protein absorption into the cell between 30 and 40%.

Cheng, Nook, et al. *Effects of Electric Currents on ATP Generation in Rat Skin,* Clin Ortho and Rel Res. Number 171, Nov.-Dec. (1982);

Parkenson, W. C. and C. T. Hanks, *Response of Primary and Transformed Cells to Electromagnetic Fields,* Ionic Currents, Allen R. Ilas, Inc. 329-336 (1986); and Picker, Robert, *Micro Electrical Neuromuscular Stimulation,* The American Chiropracter. Vol. 1(2) 572-574 (1987).

During electrical stimulation of pathological tissue, the electrons react with water molecules at the cathode side to produce hydroxyl ions, while at the anode side, protons are formed. Thus, between the anode and cathode interface, a proton gradient and a potential gradient across the tissue and the medium are created. Hence, protons under the influence of the electric field and the concentration difference should move from anode to cathode. Since the rate of proton formation at the anodic interface is equal to the rate of proton consumption at the cathodic interface, the net PH of the system, medium and tissue, remains undisturbed. As the migrating protons reach the mitochondrial membrane-bound ATPase, ADP will be formed.

Thus, electrical current can pass through the membrane capacitance, even though ions cannot. And so, by increasing the cell's potential, we increase the cell's own ability to produce energy.

Thus, we may use low voltage electrical fields to penetrate the protein envelope of the Herpes virus, stimulate the cell capacitance via the increase of mitochondrial function, return the cell to normal functioning, and break up the polypeptide structure of the virus core. In other words, the low DC voltage field helps the infected body cell break apart and expel the virus causing the virus to retreat to its own protein shell containing its molecule of nucleic acid where it remains in the dormant state until it finds another "weak" cell to infect. The virus does not appear to be killed, but rather forced to return to the dormant state.

A small low voltage electrical device as described and shown in connection with FIG. 1, delivers a current, barely noticeable by the subject, to the potential/actual lesion site to effect this desired action.

The following Clinical studies were carried on over a period of five years and demonstrate the unexpected, beneficial results achieved by the present method and apparatus.

EXAMPLES

Ninety-six men and women between the ages of 19 and 37 participated in the study which took place over a period of years of clinical trials. The trials were grouped in two phases. In Phase One, groups 1 and 2 below were treated four times a week for three months. A monthly clinical follow-up was continued for six months after the treatment trial period.

In Phase 2, group 3 was treated for three months as indicated below and were clinically seen once a week during this trial. A monthly clinical follow-up was again continued for six months.

Subjects were placed in one of three groups as follows:

Group One—23 controls. These subjects were administered no electrical stimulation. Some of these subjects sporadically used some form of drug therapy.

Group Two—50 subjects who were seen in a medical clinic with their treatment supervised by a medical doctor. These patients took no drugs and were treated solely with electrical stimulation.

Group Three—23 subjects who were each issued a small electrical stimulation device as shown in FIGS. 1 and 2.

All of the subjects in this study suffered from either Herpes Simplex 1 (mouth herpes), or Herpes Simplex 2 (genital herpes). Prior onset of the disease ranged from 1.5 to 5 years.

METHODS OF TREATMENT

GROUP One subjects reported onset, progress, and resolve of their lesions on a daily basis.

GROUP Two subjects were treated in the clinic commencing with the onset of the lesion and four times a week until the lesion resolved. Treatment consisted of the application of low voltage electrical stimulation delivered to the lesion by the use of a non-invasive stainless steel probe.

GROUP Three subjects were issued low voltage electrical stimulators (FIG. 1) and told to take them with them and keep them handy at all times. These subjects were further instructed to be acutely aware of the onset of the next occurrence of itching, tingling, pain, or ache in the area. They were further instructed that it was crucial that they be not only aware of the onset, but immediately be able to access the stimulation unit and use it at the site of the potential lesion as follows: "Use the electrical stimulator to make contact with the potential lesion site for 15 seconds. Continue this procedure once per hour for eight hours without interruption on the first day of recognition of preliminary symptoms." These subjects were further told that if a lesion should begin to occur, that they should continue this procedure until the lesion resolve itself.

RESULTS

The results of this study are outlined in Table 1.1

TABLE 1.1

| COMPARISON OF TREATMENT PROCEDURES | | | |
|---|---|---|---|
| HERPES SIMPLEX 1 | | HERPES SIMPLEX 2 | |
| Days w/ Lesions | No. of Patients | Days w/ Lesions | No. of Patients |
| GROUP I - Controls | | | |
| Men | 9 | 10 | 6 |
| Women | 7 | 8 | 6 |
| [Total Patients = 23 - Average Days w/Lesions 8.5] | | | |
| GROUP II - Clinically Treated | | | |
| Men | 3 | 12 | 4 |
| Women | 4 | 3 | 10 |
| [Total Patients = 50 - Average Days w/Lesions 3.5] | | | |
| GROUP III - Self-Treated | | | |
| Men | 0 | 0 | 4 |
| Women | 0 | 1 | 8 |
| [Total Patients = 23 - Average Days w/Lesions .25] | | | |

| COMPARISON OF TREATMENT PROCEDURES | | | |
|---|---|---|---|
| HERPES SIMPLEX 1 | | HERPES SIMPLEX 2 | |
| Days w/ Lesions | No. of Patients | Days w/ Lesions | No. of Patients |
| GROUP I - Controls | | | |
| Men | 9 | 7 | 10 | 6 |
| Women | 7 | 4 | 8 | 6 |

As can be seen, the three groups studied were compared as to sex, number of days of persistence of the lesion, and type of herpes.

The most successful treatment group were those subjects who treated themselves with a portable electrical stimulator as shown in FIG. 1 prior to onset of the lesion. Average length of lesion for this group was 0.25 days. It also appears that the sooner treatment starts after symptoms, the better the results. To prevent lesion formation treatment within the first twelve hours appears mandatory.

Group Two, or the clinically treated subjects averaged 3.5 days of persistence of lesion.

Group One controls fared the worst in comparison with the treatment groups. Average length of lesion for this group was 8.5 days.

A three-way analysis of variance was performed in order to compare the results of the three groups. When compared with the control group, both the clinically-treated and the self-treated groups demonstrated a shorter time of persistence significant at the 0.001 level. The self treated group demonstrated an even more significant reduction in time of lesion persistence than the clinically-treated group at the 0.001 level.

The data presented, demonstrates that low voltage electrical current, when applied to the lesion site, can significantly reduce the time of persistence of that lesion resulting from either Herpes Simplex 1 or 2.

The data further demonstrates, even more dramatically, the self-treatment with low voltage electrical current within the first 15 minutes of the occurrence of a Herpes Simplex symptom, can prevent the occurrence of a lesion at the site of stimulation.

Finally, the data indicates that there was no significant difference in results of treatment with regard to sex or type of Simplex manifested.

CONCLUSION

Low voltage electrical current, when applied to the lesion site, or a possible lesion site, appears to penetrate the protein envelope barrier which protects the virus from destruction. As the herpesvirus manifests itself via the nervous system, a treatment route is provided to pervade the system and attack the virus using the electrical properties of the nervous system at the cell level, to combat the virus.

An electrical current can radically change the response of the healthy cell to the invading virus. This appears to be accomplished by stimulating the mitochondrial function of the cell to return to normal the ionic balance inside and outside the cell. The foregoing clinical study has been an example of the electrical manipulation of the biochemistry of pathological cells in a viral medium. It was found that both pathological cells and virus are affected to a significant extent with the application of low voltage electrical stimulation at the site of that interaction. The most significant affect appears to be created by the treatment of a virus produced pathological state at the onset, whereby the virus has not had an opportunity to fully invade the system, or reach its fullest strength.

The key to effective treatment of the herpesvirus, whether it is Herpes Simplex 1 or Herpes Simplex 2, is the beginning of treatment by low voltage electrical stimulation at the possible site of a lesion, as indicated by tingling or other pre-lesion symptoms, as soon as the symptoms are felt. Delay beyond the first 12–18 hours after the first symptoms will usually result in lesions occurring, although if treated, the duration is greatly reduced.

While this invention has been explained with reference to the structure disclosed herein, it is not confined to the details as set forth and this application is intended to cover any modifications and changes as may come within the scope of the following claims.

BIBLIOGRAPHY

Barr, Murry L. *The Human Nervous System.* Harper and Row, 1974.

Barron, Jesse J., et. al. (1985) Treatment of decubitus ulcers. *Minnesota Medicine.* (Feb) 103–106.

Becker, Robert O. *The Body Electric,* William Morrow Inc., New York, N.Y. 1985.

Becker, Robert O. (1974) Data transmission and control, *Annals New York Academy of Sciences,* Syracuse, N.Y.

Black, Jonathon, (1984) Tissue response to exogenous electromagnetic signals, *Orthopedic Clinics of North America.* Vol. 15. No. 1.

Bogatyryov, Vladenir, *Soviet Life,* "Treating Diseases Without Drugs," No. 3, (258), Mar. 1978. [Reprints from: A Summary of Research in Biostimulation]

Borgens, Richard B. (1986) Roll of natural and applied electric fields in neuronal regeneration. *Ionic Currents,* Allen R. Liss, Inc. 239–250.

Borgens, Richard B. (1986) Transsected dorsal column axons within the guinea pig spinal cord regenerate in applied electric field. *J. Comp. Neur.* 250: 168–180.

Carley, Patrick J. and Stanley F. Warnapel, (1986) Electrotherapy for acceleration of wound healing:

low intensity direct current. *Arch Phys Med Rehabil.* Vol. 66 443–446.

Cheng, Nook, et. al. (1982) Effects of electric currents on ATP generation in rat skin. *Clin Ortho and Rel Res.* Number 171, Nov.–Dec.

Cochran, G. V. B. et. al. (1985) Piezo electric internal fixation devices: a new approach to electrical augmentation of osteogenisis. *J. Orthopedic Res.* 3: 508–513.

Colacicco, G. and Arthur A. Pilla. (1983) Electromagnetic modulation of biological processes. *Z. Naturforsch.* 38c, 468–470.

Darnell, James, and Harvey Lodish, and David Baltimore, *Molecular Cell Biology.* New York, N.Y.; Scientific American Books, 1986.

Forgen, M. et. al. (1985) Bone growth accelerated by stimulation of the epiphyseal plate with electric current. *Arch Ortho Trama Surg.* 104: 121–124.

Freeman, J. A. et. al. (1985) Steady growth cone currents. *J. Neur. Res.* 13: 257–283.

Goldstein A. (1976) Opioid peptides (endorphins) in pituitary and brain. *Science.* 193 1081–1086.

Guillemin R. (1977) Endorphins, brain peptides that act like opiates. *N Engl. J. Med.* 1: 226–228.

Hudlicka, O., et. al. (1977). The effects of long-term stimulation of fast muscles on their blood flow and metabolism. *Pftugers Arch.* 369. 141–149.

Jewett, L., et. al., *Basic Concepts of Neuronal Function,* Little, Brown, and Co., Boston, Mass. 1984.

Kenyon, Julian M. (1979) Bioelectric potentials and their relation to acupuncture. *Acupuncture and Electro-Therapeut. Res., Int. J.* 4: 37–41.

Kroetlinger, Michael. (1980) On the use of the laser in acupuncture. *Acupuncture and Electro-Therapeutics Res., Int. J.,* Vol. 5, pp. 297–311.

Lehninger, Albert L., *Principles of Biochemistry,* New York, N.Y.; Worth Publishers, Inc, 1982.

Luttgens, Kathryne, and Katherine F. Wells, *Kinesiology,* New York N.Y.; Saunders College Publishing, 1982.

McAuliffe, Kathleen, (1980) I sing the body electric. *Omni.* Nov., 70–98.

McCaig, Colin D. (1986) Electric fields, contact guidance and the direction of nerve growth. *J. Embryol. exp. Morph.* 94: 245–255.

Nelson, Roger M., and Dean P. Currier, *Clinical Electrotherapy.* Norwalk, Conn.; Appleton and Lange, 1987.

Parkenson, W. C. and C. T. Hanks, (1986) Response of primary and transformed cells to electromagnetic fields, *Ionic Currents.* Allen R. Liss, Inc. 329–336.

Patel, Nilesh and Mu-Ming Poo. (1982) Orientation of neurite growth by extracellular electric fields. *J. Neuroscience,* Vol. 2. No. 4, pp. 483–496.

Pette, Dirk, et. al. (1973) Effects of long-term stimulation of fast rabbit muscles. *Pflugers Arch.* 338: 257–272.

Picker, Robert, (1987) Micro electrical neuromuscular stimulation. *The American Chiropracter.* Vol. 1(2) 572–574.

Pilla, Arthur A. (1974) Electrochemical information transfer. *Annals New York Academy of Sciences.* 138–167.

Purves, William K. and Gordian H. Orians, *Life: The Science of Biology,* Sinauer Ass., Sunderland, Mass. 1983.

Robinson, K. R. and R. F. Stump. (1984) Self-generated electrical current through *Xenopus neuralae. J. Physiol.* 352: 339–352.

Royal, F. Fuller, and Craig K. Mayfield. *Physicians Electro-Diagnostic Handbook,* Nevada Clinic of Preventive Medicine. L. V. Nevada, 1983.

Schmidt, Robert, Ed. *Fundamentals of Neurophysiology,* Springer Verlag, 1978.

Sears, Francis W., *University Physics.* Reading, Mass.: Addison-Wesley Pub. Co., 1982.

Travell, Janet G., and David G. Simons, *Myofascial Pain and Dysfunction: The Trigger Point Manual,* Williams and Wilkins, Baltimore/London, 1983.

Wall, Patrick, and Ronald Melzack, *Textbook of Pain.* New York, N.Y.; Churchill Livingstone, 1984.

Waters, Robert L., et. al. *Functional Electrical Stimulation.* Downey, Ca.: Professional Staff Ass., 1981.

Wing, Thomas W. (1984) Trigger point therapy. *Digest of Chiro. Econ.* 78–81. Mar./Apr.

Wolbarsht, M. L., Ed. *Laser Applications in Medicine and Biology.* Plenum Press, N.Y. Vol. 3, 1977. [Reprints from: A Summary of Research in Biostimulation].

What is claimed is:

1. The method of treating herpes virus infections of the human body by
   inhibiting viral infections of healthy cells and the development of virus infected cells which comprises:
   applying a low voltage DC current to the skin immediately adjacent the symptom site to penetrate the protein envelope of the Herpes virus infected cell,
   break up the polypeptide structure of the virus core and disperse the lipid proteins;
   increasing the mitochondrial function of the herpes virus infected cells and the healthy cells to restore cell capacitance to normal, thereby preventing development of the Herpes virus.

2. The method of claim 1 further defined by applying the defined therapeutic steps repeatedly at hourly intervals for very limited time durations of two to fifteen seconds for at least eight hours after onset of symptoms.

3. The method of claim 2 further defined by applying the electrical field to the skin at two points spaced apart a distance of one-half inch to one-and-one-half inches.

4. The method of claim 3 further defined by applying a nine volt DC field to the skin of the tissue under virus attack to cause a small milliampere current to flow through the cells in the tissue adjacent the virus attack zone.

5. In the treatment of the symptoms of Herpes Simplex 1 and 2, the method of inhibiting development of herpetic lesions in the human body upon occurrence of precursor symptoms which comprises:
   applying a low DC electrical voltage directly to the body at the site of the precursor symptoms of developing herpes virus lesions;
   applying said DC voltage for a very short period of time of less than one minute;
   repeating the application of said DC voltage at regular intervals of time of less than two hours over an extended period of time until the precursor symptoms disappear.

6. The method of claim 5 further defined by applying a DC voltage to the body for a duration of 3 to 20 seconds at intervals between 45 minutes and 75 minutes.

7. The method of claim 6 further defined by applying said low voltage to the skin at two points spaced apart a distance of one-half inch to one-and-one-half inches.

8. The method of claim 5 including applying said voltage initially within fifteen minutes of the onset of symptoms.

9. The method of claim 5 further defined by:
applying a nine volt DC voltage to the skin within fifteen minutes of the onset of symptoms; and
applying said DC voltage periodically at intervals of approximately one hour for a duration of approximately 15 seconds over a period of at least eight hours.

10. The method of treating Herpes Simplex 1 and 2 virus infections of the human body which cause lesions to appear on the skin which comprises the steps of:
applying a low DC voltage directly to the body skin at the site of the virus lesions;
applying said DC voltage for a very short time duration of less than one minute;
repeating the application of said DC voltage at regular intervals of less than two hours; and
continuing the periodic application of said DC voltage for at least eight hours or until the lesions heal.

11. The method of claim 10 including applying said voltage initially within fifteen minutes of the onset of symptoms and continuing the periodic application of said DC voltage for at least twenty-four hours.

12. The method of claim 10 further defined by applying said DC voltage for a duration of 3 to 20 seconds at intervals between 45 minutes and 75 minutes.

13. The method of claim 12 further defined by applying the voltage to the skin at two points spaced apart a distance of three quarters to one-and-one-half inches.

14. The method of treating herpes virus lesions on the human body by inhibiting viral infections of healthy cells and further development of virus infected cells through increasing the mitochondrial function of the cells to stimulate both infected and healthy cells to normal functioning, which comprises:
applying a constant low voltage DC current to the skin immediately adjacent the symptom site;
applying said DC current repeatedly at regular intervals for durations of less than one minute at intervals of less than two hours; and
continuing said application of DC current for an extended period of time of at least eight hours;
thereby causing the affected cells to increase ATP production and thus cell energy so as to stimulate cellular inactivation of the herpes virus in infected cells and the rejection thereof by healthy cells.

* * * * *

UNITED STATES PATENT AND TRADEMARK OFFICE
CERTIFICATE OF CORRECTION

PATENT NO. : 5,133,352
DATED : July 28, 1992
INVENTOR(S) : Lathrop et al

It is certified that error appears in the above-indentified patent and that said Letters Patent is hereby corrected as shown below:

On the title page, item [73] Assignee: should read as follows:

-- [73] Assignee: Peter H. Lathrop and Steven K. Johbston, San Diego, Calif.--.

Signed and Sealed this

Seventh Day of December, 1993

Attest:

BRUCE LEHMAN

*Attesting Officer*  *Commissioner of Patents and Trademarks*

(12) EX PARTE REEXAMINATION CERTIFICATE (5988th)
United States Patent
Lathrop et al.

(10) Number: US 5,133,352 C1
(45) Certificate Issued: Nov. 6, 2007

(54) METHOD FOR TREATING HERPES SIMPLEX

(75) Inventors: Peter H. Lathrop, San Diego, CA (US); Steve K. Johnston, Grand Island, NE (US)

(73) Assignee: Nexmed Holdings, Inc., Commerce, CA (US)

Reexamination Request:
No. 90/007,855, Dec. 20, 2005

Reexamination Certificate for:
Patent No.: 5,133,352
Issued: Jul. 28, 1992
Appl. No.: 07/508,840
Filed: Apr. 12, 1990

Certificate of Correction issued Dec. 7, 1993.

(51) Int. Cl.
*A61N 1/20* (2006.01)

(52) U.S. Cl. ......................................................... 607/75
(58) Field of Classification Search ................. 607/72, 607/75
See application file for complete search history.

(56) References Cited

U.S. PATENT DOCUMENTS

| | | |
|---|---|---|
| 2,099,511 A | 11/1937 | Caesar |
| 3,549,770 A | 12/1970 | Herschler |
| 3,725,226 A | 4/1973 | Stoner |
| 3,773,049 A | 11/1973 | Rabichev |
| 3,924,641 A | 12/1975 | Weiss |
| 4,541,432 A | 9/1985 | Molina-Negro et al. |
| 4,702,732 A | 10/1987 | Powers |
| 4,786,277 A | 11/1988 | Powers |
| 4,895,154 A | 1/1990 | Bartelt et al. |
| 4,913,148 A * | 4/1990 | Diethelm .................... 607/72 |

\* cited by examiner

*Primary Examiner*—Jimmy G. Foster (57) ABSTRACT

The present invention provides an apparatus and method for treating infectious skin conditions, such as Herpes Simplex 1 and 2. By the application of an electrical field and current to the area of the manifestation of the disease on the body there is activated a reaction at the cell level to combat the virus and disrupt its attack on the healthy cell structure. The present method comprises a direct application of a low voltage direct current, low amperage stimulation to the skin about the infected location for a few seconds every hour for a length of time sufficient to prevent formation and/or heal the resultant lesion.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 6 and 12 are cancelled.

Claims 1, 3, 5, 7, 10, 13 and 14 are determined to be patentable as amended.

Claims 4, 8, 9 and 11, dependent on an amended claim, are determined to be patentable.

1. The method of treating herpes virus infections of the human body by
    inhibiting viral infections of healthy cells and development of virus infected cells which comprises:
    applying a low voltage DC current to the skin *at two points spaced apart a distance of one-half inch to one-and-one-half inches* immediately adjacent the symptom site to penetrate the protein envelope of the Herpes virus infected cell,
    break up the polypeptide structure of the virus core and disperse the lipid proteins;
    increasing the mitochondrial function of the herpes virus infected cells and the healthy cells to restore cell capacitance to normal, thereby preventing development of the Herpes virus.

3. [The method of claim 2 further defined by applying the electrical field] *The method of treating Herpes virus infections of the human body by inhibiting viral infections of healthy cells and the development of virus infected cells which comprises:*
    applying repeatedly, at hourly intervals for time durations of two to fifteen seconds for at least eight hours, after onset of symptoms, a low voltage DC current to the skin at two points spaced apart a distance of one-half inch to one-and-one-half inches *immediately adjacent the symptom site to penetrate the protein envelope of the Herpes virus infected cell,*
    *break up the polypeptide structure of the virus core and disperse the lipid proteins;*
    *increasing the mitochondrial function of the Herpes virus infected cells and the healthy cells to restore cell capacitance to normal, thereby preventing development of the Herpes virus.*

5. In the treatment of the symptoms of Herpes Simplex 1 and 2, the method of inhibiting development of herpetic lesions in the human body upon occurrence of precursor symptoms which comprises:
    applying a low DC electrical voltage directly to the body at the site of the precursor symptoms of developing herpes virus lesions *at two points spaced apart a distance of one-half inch to one-and-one-half inches*;
    applying said DC voltage for a very short period of time of less than one minute;
    repeating the application of said DC voltage at regular intervals of time of less than two hours over an extended period of time until the precursor symptoms disappear.

7. [The method of claim 6 further defined by applying said low voltage to the skin] *In the treatment of the symptoms of Herpes Simplex 1 and 2, the method of inhibiting development of herpetic lesions in the human body upon occurrence of precursor symptoms which comprises:*
    applying a low DC electrical voltage directly to the body at the site of the precursor symptoms of developing herpes virus lesions at two points spaced apart a distance of one-half inch to one-and-one-half inches;
    *applying said DC voltage for a duration of 3 to 20 seconds at intervals between 45 minutes and 75 minutes;*
    *repeating the application of said DC voltage at regular intervals of time of less than two hours over an extended period of time until the precursor symptoms disappear.*

10. The method of treating Herpes Simplex 1 and 2 virus infections of the human body which cause lesions to appear on the skin which comprises the steps of:
    applying a low DC voltage directly to the body skin at the site of the virus lesions *at two points spaced apart a distance of one-half inch to one-and-one-half inches*;
    applying said DC voltage for a very short time duration of less than one minute;
    repeating the application of said DC voltage at regular intervals of less than two hours; and
    continuing the periodic application of said DC voltage for at least eight hours or until the lesions heal.

13. [The method of claim 12 further defined by applying the voltage to the skin] *The method of treating Herpes Simplex 1 and 2 virus infections of the human body which cause lesions to appear on the skin in accordance with claim 10 which comprises the steps of:*
    *applying a low DC voltage directly to the body skin at the site of the virus lesions* at two points spaced apart a distance of three quarters to one-and-one-half inches;
    *applying said DC voltage for a duration of 3 to 20 seconds at intervals between 45 minutes and 75 minutes.*

14. The method of treating herpes virus lesions on the human body by inhibiting viral infections of healthy cells and further development of virus infected cells through increasing the mitochondrial function of the cells to stimulate both infected and healthy cells to normal functioning, which comprises:
    applying a constant low voltage DC current to the skin *at two points spaced apart a distance of one-half inch to one-and-one-half inches* immediately adjacent the symptom site;
    applying said DC current repeatedly at regular intervals for durations of less than one minute at intervals of less than two hours; and
    continuing said application of DC current for an extended period of time of at least eight hours;
    thereby causing the affected cells to increase ATP production and thus cell energy so as to stimulate cellular inactivation of the herpes virus in infected cells and the rejection thereof by healthy cells.

* * * * *

US005133352C2

(12) EX PARTE REEXAMINATION CERTIFICATE (6835th)
United States Patent
Lathrop et al.

(10) Number: US 5,133,352 C2
(45) Certificate Issued: May 19, 2009

(54) METHOD FOR TREATING HERPES SIMPLEX (75) Inventors: Peter H. Lathrop, San Diego, CA (US); Steve K. Johnston, Grand Island, NE (US)

(73) Assignee: Nexmed Holdings, Inc., Commerce, CA (US)

Reexamination Request:
No. 90/008,923, Nov. 15, 2007

Reexamination Certificate for:
Patent No.: 5,133,352
Issued: Jul. 28, 1992
Appl. No.: 07/508,840
Filed: Apr. 12, 1990

Reexamination Certificate C1 5,133,352 issued Nov. 6, 2007

Certificate of Correction issued Dec. 7, 1993.

(51) Int. Cl.
*A61N 1/20* (2006.01)

(52) U.S. Cl. .......................................................... 607/75
(58) Field of Classification Search ........................ None
See application file for complete search history.

(56) References Cited

U.S. PATENT DOCUMENTS

| 305,894 A | 9/1884 | Clarke |
| 1,433,184 A | 10/1922 | Csanyi |
| 3,918,459 A | 11/1975 | Horn |
| 4,181,128 A | 1/1980 | Swartz |
| 4,233,986 A | 11/1980 | Tannenbaum |
| 4,913,148 A | 4/1990 | Diethelm |

OTHER PUBLICATIONS

Wolcott, Wheeler, Hardwicke, Rowley, Accelerated Healing of Skin Ulcers By Electrotherapy *Southerm Medical Journal*, 62(7):795–801, Southern Medical Association, Jul. 1969.
Nathan, Wall, Treatment of Post–Herpetic Neuralgia By Prolonged Electric Stimulation *British Medical Journal*, 3, pp. 645–647, Sep. 1974.

*Primary Examiner*—Jeffrey R. Jastrzab (57) ABSTRACT

The present invention provides an apparatus and method for treating infectious skin conditions, such as Herpes Simplex 1 and 2. By the application of an electrical field and current to the area of the manifestation of the disease on the body there is activated a reaction at the cell level to combat the virus and disrupt its attack on the healthy cell structure. The present method comprises a direct application of a low voltage direct current, low amperage stimulation to the skin about the infected location for a few seconds every hour for a length of time sufficient to prevent formation and/or heal the resultant lesion.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1, 3–5, 7–11, 13 and 14 is confirmed.

Claims 2, 6 and 12 were previously cancelled.

* * * * *